United States Patent
Mandula et al.

(10) Patent No.: US 10,545,329 B2
(45) Date of Patent: Jan. 28, 2020

(54) DEVICE AND METHOD FOR OBSERVING A SAMPLE WITH A CHROMATIC OPTICAL SYSTEM

(71) Applicant: Commissariat a l'energie atomique et aux energies alternatives, Paris (FR)

(72) Inventors: Ondrej Mandula, Grenoble (FR); Cedric Allier, Grenoble (FR)

(73) Assignee: Commissariat a l'energie atomique et aux energies alternatives, Paris (FR)

( * ) Notice: Subject to any disclaimer, the term of this patent is extended or adjusted under 35 U.S.C. 154(b) by 0 days.

(21) Appl. No.: 16/223,511

(22) Filed: Dec. 18, 2018

(65) Prior Publication Data
US 2019/0187453 A1    Jun. 20, 2019

(30) Foreign Application Priority Data
Dec. 18, 2017    (FR) ...................................... 17 62390

(51) Int. Cl.
*H04N 7/18*    (2006.01)
*G02B 21/36*    (2006.01)
(Continued)

(52) U.S. Cl.
CPC ....... *G02B 21/367* (2013.01); *G01N 21/6458* (2013.01); *G01N 21/6486* (2013.01);
(Continued)

(58) Field of Classification Search
CPC .................................................. G02B 21/367
(Continued)

(56) References Cited

U.S. PATENT DOCUMENTS 5,252,834 A * 10/1993 Lin ..................... G01N 21/6408
250/458.1
5,784,162 A * 7/1998 Cabib .................. C12Q 1/6841
250/461.2

(Continued)

FOREIGN PATENT DOCUMENTS

EP          1 406 081 A1     4/2004
WO    WO 2015/038967 A1    3/2015

OTHER PUBLICATIONS

Laura Waller et al.. "Phase from Chromatic Aberrations", Optics Express, vol. 18, No. 22, Oct. 25, 2010, 9 pages.

(Continued)

*Primary Examiner* — Leron Beck
(74) *Attorney, Agent, or Firm* — Oblon, McClelland, Maier & Neustadt, L.L.P.

(57) ABSTRACT

The invention relates to a method for observing a fluorescent sample lying in a sample plane, where the sample comprises a fluorescent agent able to emit a fluorescence light wave in a fluorescence spectral band when it is illuminated by an excitation light wave, in an excitation spectral band. The method includes illuminating the sample using a first light source, in a first illumination spectral band in the excitation spectral band, and acquiring a first image of the sample, in the fluorescence spectral band, using an image sensor; and illuminating the sample using a second light source, in a second spectral band, outside of the fluorescence spectral band, and acquiring a second image of the sample, in the second spectral band, using the image sensor. The image sensor is coupled to an optical system such that in the fluorescence spectral band, the object focal plane of the optical system is coincident with the plane of the sample; and in the second spectral band, the object focal plane of the (Continued)

optical system is offset with respect to the plane of the sample.

15 Claims, 9 Drawing Sheets

(51) Int. Cl.
*G01N 21/64* (2006.01)
*G02B 21/16* (2006.01)
*G02B 21/06* (2006.01)
*G06K 9/00* (2006.01)

(52) U.S. Cl.
CPC ............. *G02B 21/06* (2013.01); *G02B 21/16* (2013.01); *G06K 9/00127* (2013.01)

(58) Field of Classification Search
USPC .......................................................... 348/79
See application file for complete search history.

(56) References Cited

U.S. PATENT DOCUMENTS

| | | | | |
|---|---|---|---|---|
| 5,847,400 | A * | 12/1998 | Kain | G01N 21/6428 250/458.1 |
| 6,444,992 | B1 * | 9/2002 | Kauvar | G02B 21/16 250/458.1 |
| 10,393,661 | B2 * | 8/2019 | Dake | G01N 21/6428 |
| 2001/0048082 | A1 * | 12/2001 | Osipchuk | G02B 21/16 250/458.1 |
| 2002/0057430 | A1 * | 5/2002 | Engelhardt | B82Y 15/00 356/318 |
| 2004/0239916 | A1 | 12/2004 | Seino et al. | |
| 2005/0078362 | A1 * | 4/2005 | Borlinghaus | G02B 21/002 359/385 |
| 2005/0237605 | A1 * | 10/2005 | Vodyanoy | G02B 21/10 359/385 |
| 2011/0254943 | A1 | 10/2011 | Ozinsky et al. | |
| 2012/0292531 | A1 * | 11/2012 | Grudinin | G01N 21/6458 250/459.1 |
| 2015/0192767 | A1 * | 7/2015 | Li | G02B 21/18 348/79 |
| 2016/0334613 | A1 * | 11/2016 | Ishiwata | G02B 21/361 |

OTHER PUBLICATIONS

H. J. Tiziani et al., "Three-dimensional Image Sensing by Chromatic Confocal Microscopy", Applied Optics, vol. 33, No. 10, Apr. 1, 1994, pp. 1838-1843.
French Preliminary Search Report dated Aug. 24, 2018 in French Application 17 62390 filed on Dec. 18, 2017 (with English Translation of Categories of Cited Documents and Written Opinion).
Wang, H. et al. "Computational out-of-focus imaging increases the space-bandwidth product in lens-based coherent microscopy," OPTICA, vol. 3, No. 12, Nov. 28, 2016, 10.1364/OPTICA.3.001422, pp. 9.
https://www.essenbioscience.com/en/products/inoucyte (Website Only).

* cited by examiner

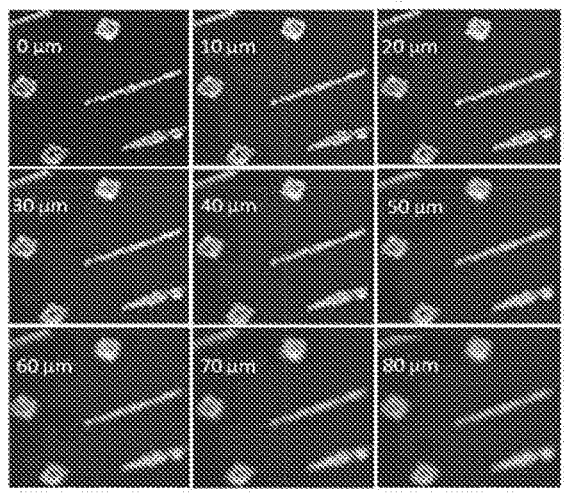
Fig. 2A
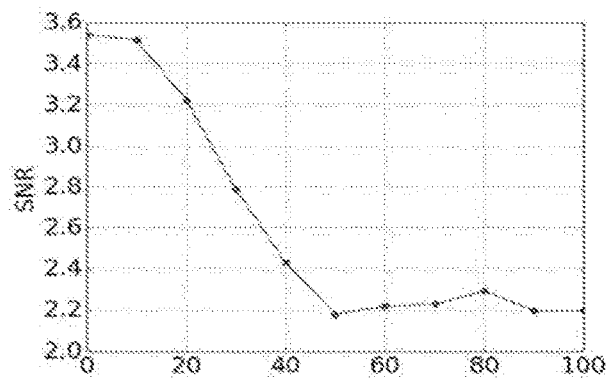
Fig. 2B
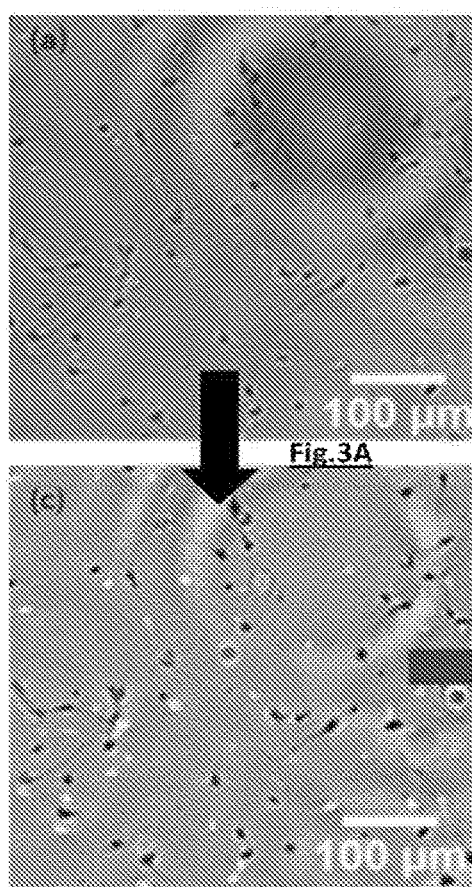
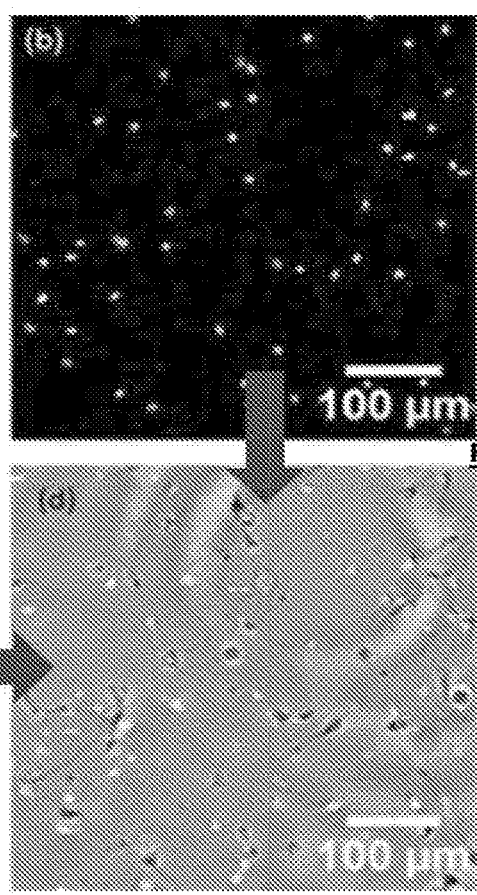
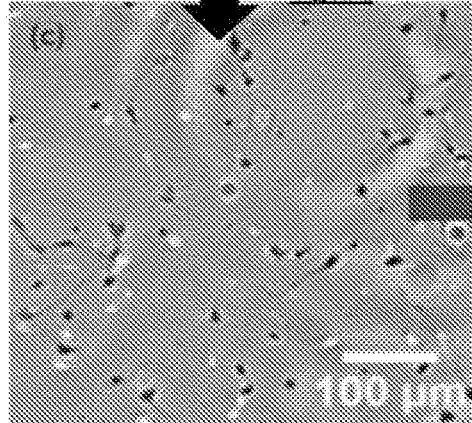
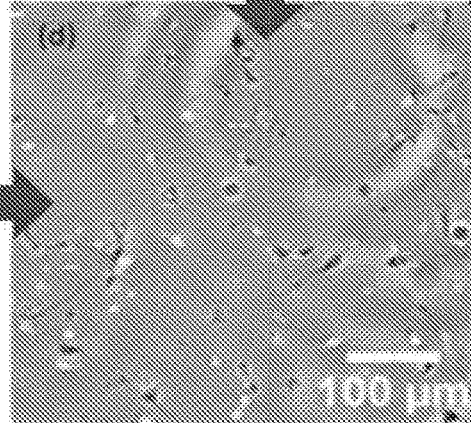
Fig. 3A
Fig. 3B
Fig. 3C
Fig. 3D

DEVICE AND METHOD FOR OBSERVING A SAMPLE WITH A CHROMATIC OPTICAL SYSTEM

TECHNICAL FIELD

The technical field of the invention is the imaging of transparent or translucent samples, especially biological samples, with a view to obtaining information relating to the structure of the sample and information relating to the fluorescence of the sample.

PRIOR ART

The application of microscopy to fluorescent samples is a very commonplace observing technique, in particular in the field of biology or medical diagnostics. When this technique is used, the sample is placed in an object focal plane of an objective, which is optically coupled to an image sensor. The sample is illuminated at an excitation wavelength, inducing a fluorescence of the sample, so as to form a fluorescence image. The sample is also illuminated at a wavelength that does not induce fluorescence, so as to form a visible image, representing the structure of the sample. The fluorescence image and the visible image are frequently superposed.

A problem arises when the sample is transparent or translucent. This situation quite frequently occurs during the observation of samples in the field of biology, for example when the sample comprises cells or microorganisms. The visible image is then not exploitable, or not sufficiently exploitable to obtain precise information on the structure of the sample.

There are however observing methods that allow an exploitable image of a transparent or translucent sample to be obtained. Specifically, when the sample is slightly defocused with respect to the optical system, it is possible to form what is called a defocused image of the sample. Since the sample is illuminated with an incident light wave, the defocused image contains information relating to the phase shift of the incident light wave by the sample. It is possible to apply holographic reconstruction algorithms to the defocused image so as to obtain what is called a reconstructed image that contains relatively precise information as to the phase shift produced by the sample. This technique is referred to as phase microscopy. The reconstructed image generally allows exploitable information on the structure of the sample to be obtained. Examples of exploitation of a defocused image are for example described in WO2016075279 or WO2016097092.

The inventors have developed a device and method for observing an object, of a design that is simple and inexpensive, that allows a fluorescent sample to be observed, and that is particularly suitable for transparent or translucent samples.

Other advantages and features will become more clearly apparent from the following description of particular embodiments of the invention, which are given by way of nonlimiting example, and shown in the figures listed below.

SUMMARY OF THE INVENTION

A first subject of the invention is a method for observing a fluorescent sample, lying in a sample plane, the sample comprising a fluorescent agent configured to emit a fluorescence light wave, in a fluorescence spectral band, when it is illuminated by an excitation light wave, in an excitation spectral band, the method comprising the following steps:

a) illuminating the sample using a first light source, in a first illumination spectral band, the first illumination spectral band lying in the excitation spectral band, and acquiring a first image of the sample, in the fluorescence spectral band, using an image sensor, the image sensor defining a detection plane;

b) illuminating the sample using a second light source, in a second spectral band, outside of the fluorescence spectral band, the sample lying between the second light source and the image sensor, and acquiring a second image of the sample, in the second spectral band, using the image sensor;

the image sensor being coupled to an optical system placed between the image sensor and the sample, the optical system being such that:

in the fluorescence spectral band, the object focal plane of the optical system is coincident with the sample plane;

in the second spectral band, the object focal plane of the optical system is offset with respect to the sample plane, and/or the image focal plane of the optical system is offset with respect to the detection plane, the offset being larger than 20 µm or larger than 30 µm;

such that:

the first image is a focused image of the sample, which image is representative of a fluorescence of the sample;

the second image is a defocused image of the sample, which image is representative of a structure of the sample.

Thus a bimodal method for observing a sample, taking advantage of the use of a chromatic optical system, and allowing a first image of the sample to be produced in a fluorescence mode and a second image of the sample to be produced in a holographic-microscopy mode, is provided. The offset is due to the chromatic aberrations of the optical system. The second image may especially be an image representative of the phase of what is called an exposure light wave, to which the image sensor is exposed during the acquisition of the second image.

The method may comprise: c) applying a reconstruction operator to the second image, so as to obtain a reconstructed image of the sample in a reconstruction plane, and in particular in the sample plane.

The second spectral band may be offset, with respect to the fluorescence spectral band, by at least 150 nm and preferably by at least 200 nm.

Preferably, the image sensor, the optical system and the sample remain stationary between the acquisition of the first image and the acquisition of the second image.

Preferably, in the second spectral band, the object focal plane is offset from the sample plane by a distance smaller than 1 mm and preferably by a distance smaller than 500 µm from the sample plane, this distance preferably being smaller than 250 µm.

The first light source may be placed in a half-space bounded by the sample plane and comprising the image sensor. Alternatively, the first light source may be placed in a half-space bounded by the sample plane and comprising the second light source.

Steps a) and b) might preferably be carried out successively, step a) being carried out before step b) or vice versa.

Preferably, in the second spectral band, the offset of the object focal plane of the optical system is larger than 50 µm. It is preferably smaller than 1 mm, or even than 500 µm. It may be comprised between 50 µm and 250 µm, the range 50 µm-150 µm being preferred.

A second subject of the invention is a device for observing a fluorescent sample, the sample being configured to emit a light wave in a fluorescence spectral band when it is illuminated in an excitation spectral band, the device comprising:

a first light source configured to emit a light wave in a first spectral band lying in an excitation spectral band of the sample;

a second light source configured to emit a light wave in a second spectral band outside of the fluorescence spectral band of the sample;

an image sensor that is optically coupled to an optical system, the image sensor defining a detection plane;

a holder intended to receive the sample, such that the sample lies in a sample plane, the latter lying between the optical system and the second light source;

the optical system defining:
in the fluorescence spectral band, a first object focal plane that is coincident with the sample plane;
in the second spectral band, a second object focal plane that is distant from the sample plane by at least 20 µm or 30 µm, or a second image focal plane that is distant from the detection plane by at least 20 µm or 30 µm;
such that the image sensor is configured to acquire, preferably without moving the sample or the image sensor or the optical system:

a clear image of the sample, in the fluorescence spectral band, when the sample is illuminated by the first light source;

a defocused image of the sample, in the second spectral band, when the sample is illuminated by the second light source.

The distance between the first object plane and the second object plane is preferably smaller than 1 mm, and preferably smaller than 500 µm or than 250 µm.

The device may comprise a processor configured to apply a holographic reconstruction operator to an image acquired by the image sensor, so as to reconstruct an image representative of the sample, in a reconstruction plane distant from a detection plane in which the image sensor lies, and preferably in the sample plane The device may comprise a filter, lying between the sample and the image sensor, having a passband, called the fluorescence passband, corresponding to the fluorescence spectral band The filter allows all or some of the light wave in the excitation spectral band to be filtered. The filter may have an auxiliary passband, distinct from the fluorescence passband, corresponding to all or some of the second spectral band. The fluorescence passband of the filter advantageously has a bandwidth narrower than 100 nm.

The first light source might be placed in a half-space bounded by the sample plane and comprising the image sensor. The first light source migt be placed in a half-space bounded by the sample plane and comprising the second light source

FIGURES

FIG. 2A shows various gradually defocused fluorescence images.

FIG. 2B is a variation in a signal-to-noise ratio (y-axis) of the images illustrated in FIG. 2A, as a function of a defocus distance (x-axis) expressed in µm.

FIGS. 3A to 3D illustrate an example of implementation of a method for observing a sample: FIG. 3A is a defocused image of the sample. FIG. 3B is a fluorescence image of the sample. FIG. 3C is an image, called a phase image, of the sample, said image being obtained by applying a holographic reconstruction operator to the defocused image of the sample. FIG. 3D is a superposition of the phase image and of the fluorescence image of the sample.

Figure 4:
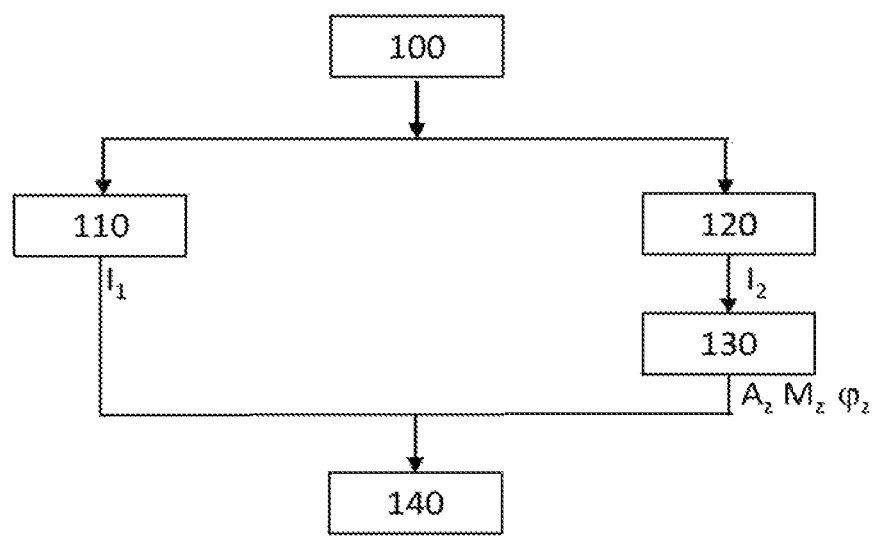

FIG. 4 shows the main steps of a method according to the invention.

Figure 5A:
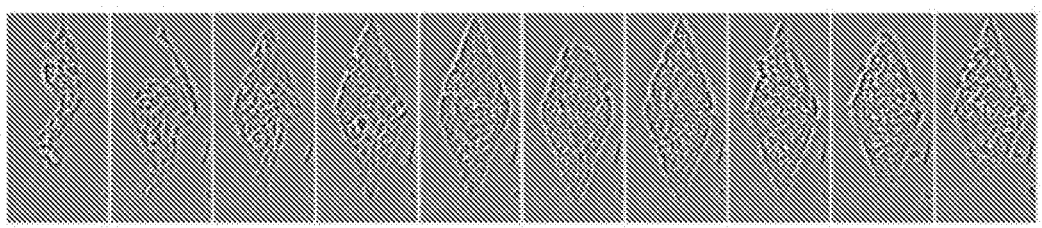
Figure 5B:
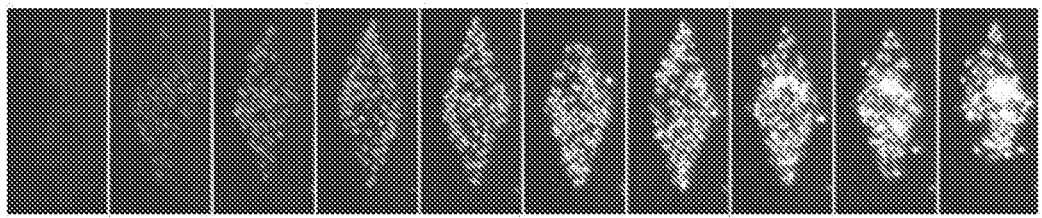
Figure 5C:
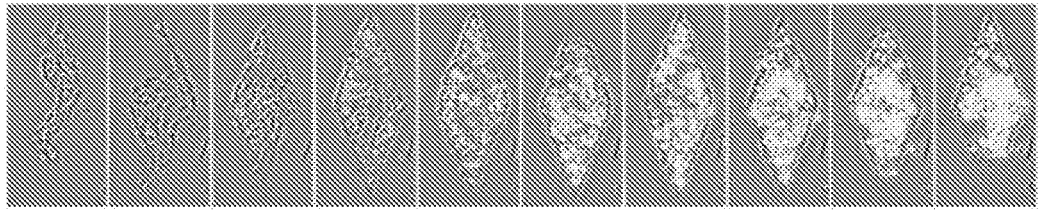

FIGS. 5A, 5B and 5C respectively show phase images, fluorescence images and superposed fluorescence and phase images, the images having been acquired regularly (every 8 hours and 20 minutes) during a time interval of 75 h.

Figure 6A:
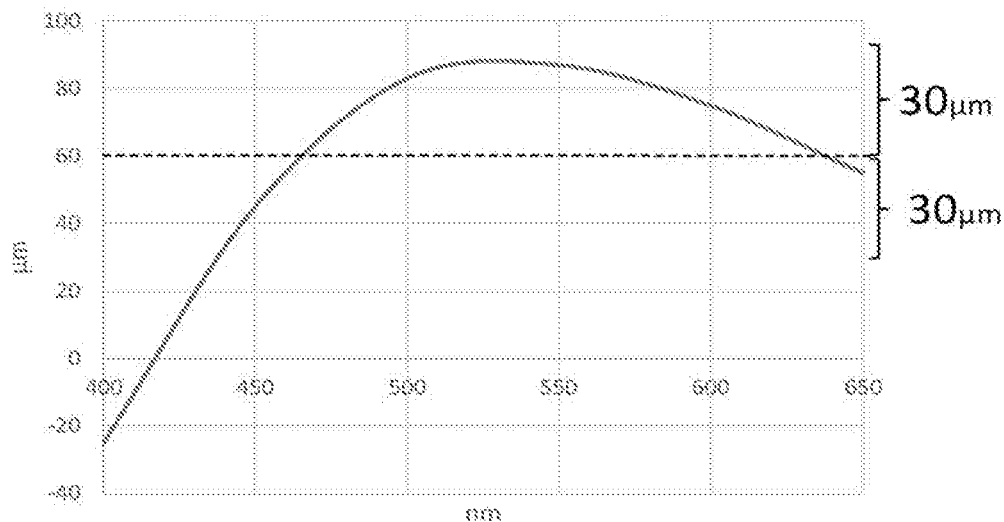

FIG. 6A shows the variation of the focal distance of an optical system as a function of the wavelenght.

Figure 6B:
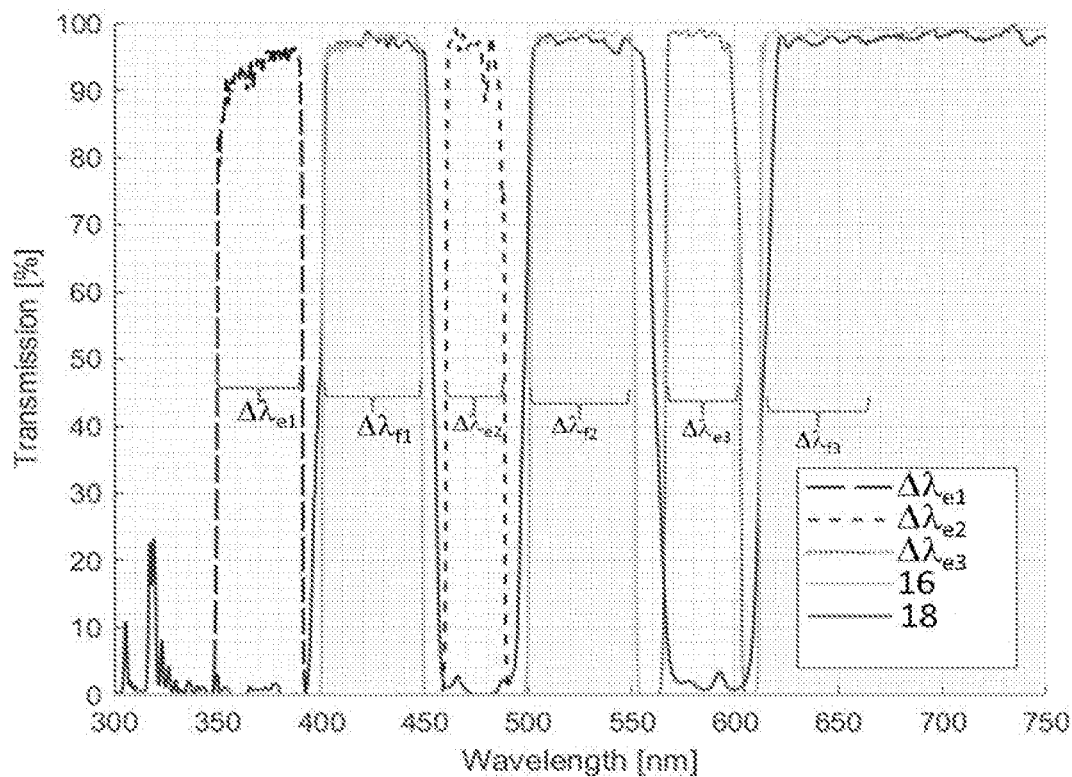

FIG. 6B shows transmission spectral bands of an excitation filter, of a dichroic mirror and of an emission filter respectively.

Figure 6C:
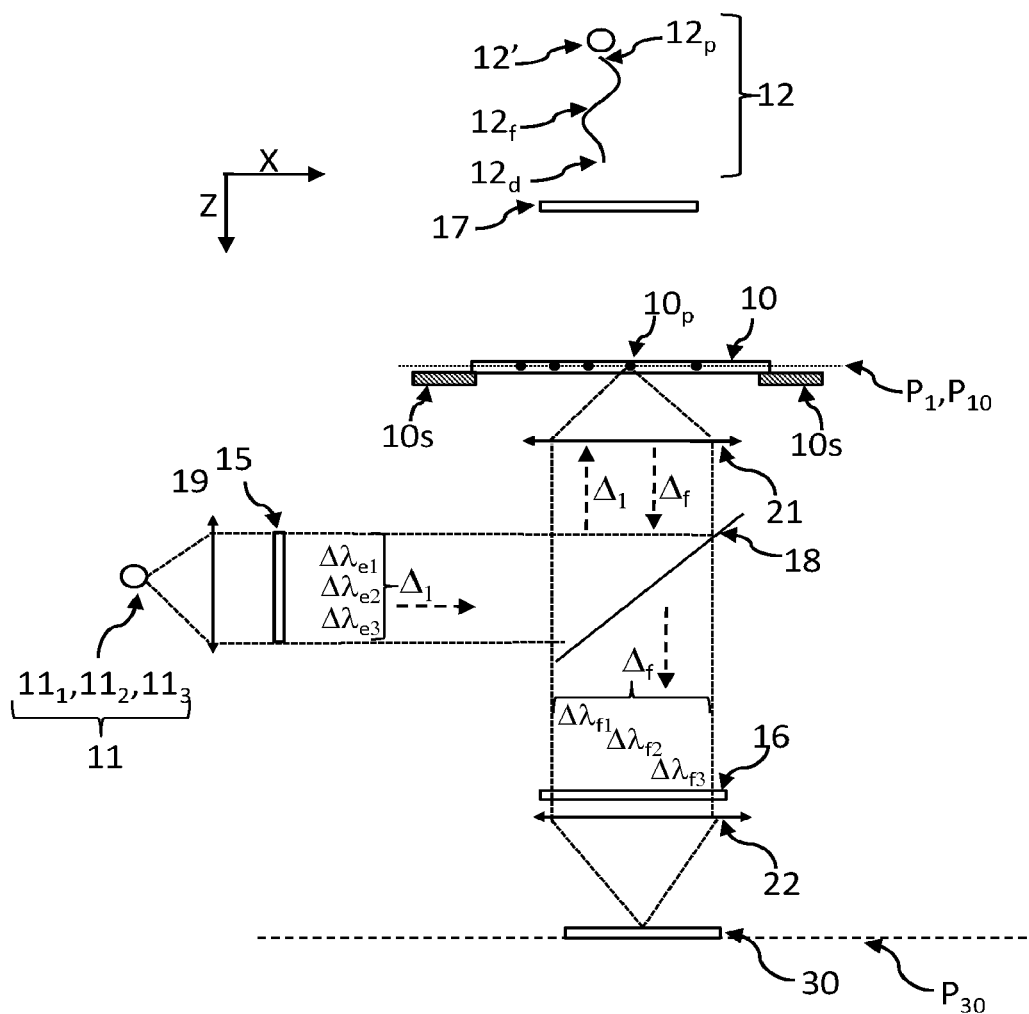

FIG. 6C shows another device of the invention in a first configuration.

Figure 6D:
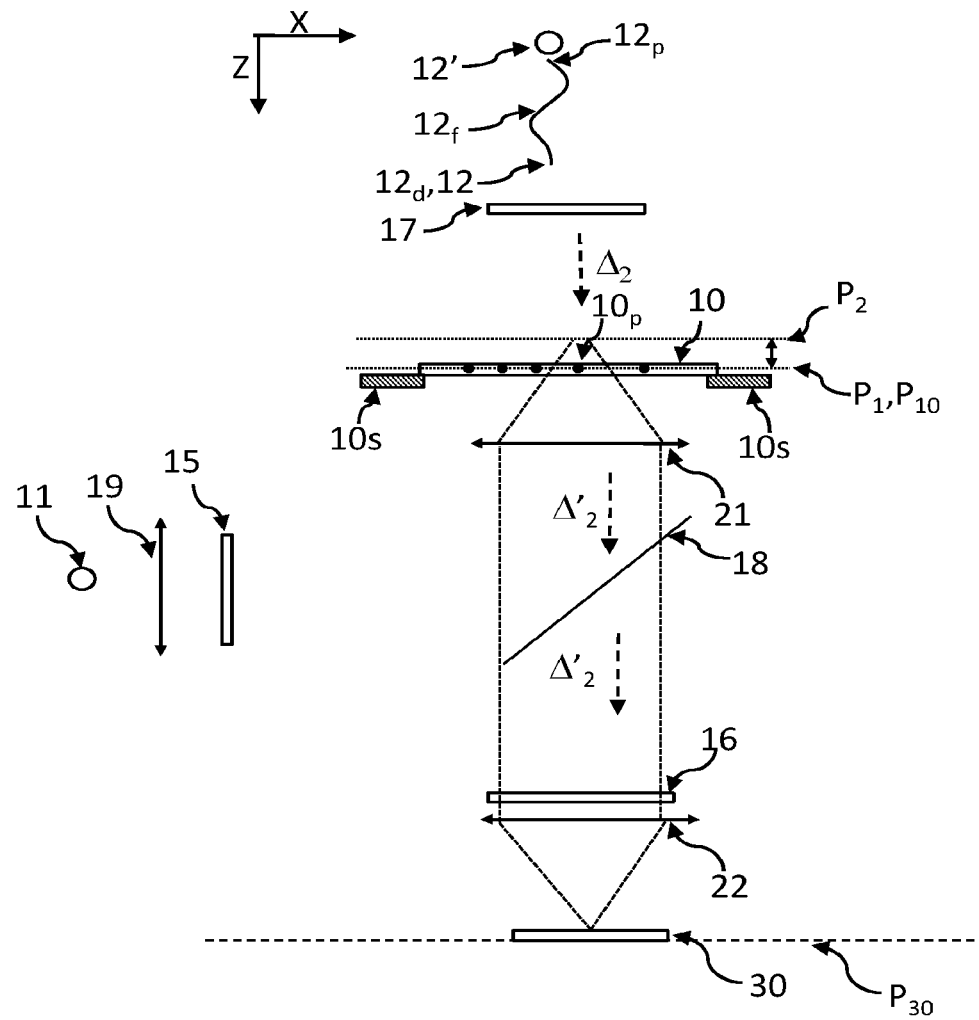

FIG. 6D shows the device shown in FIG. 6C in a second configuration.

Figure 7A:
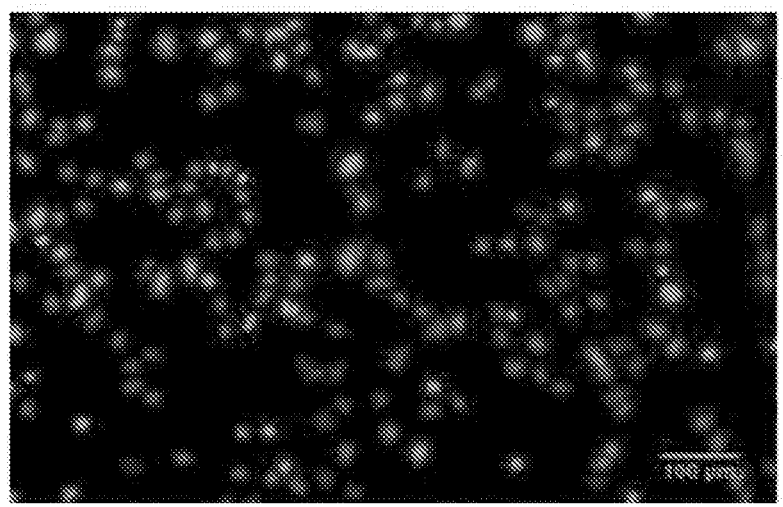
Figure 7B:
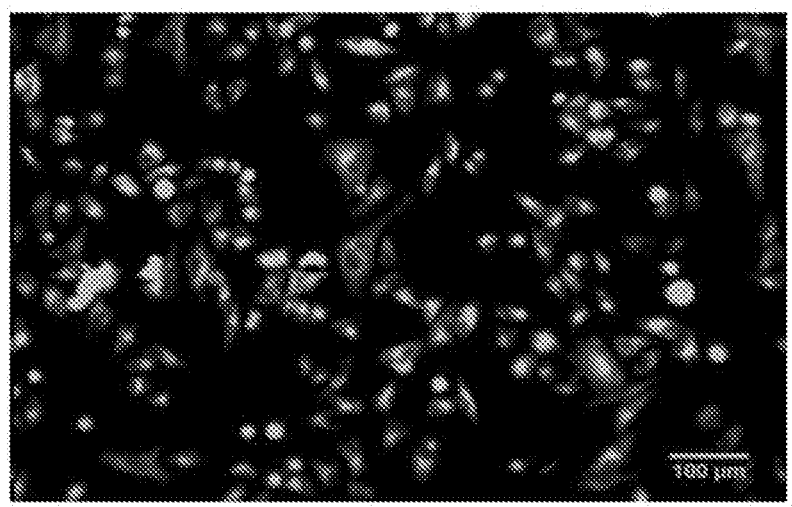
Figure 7C:
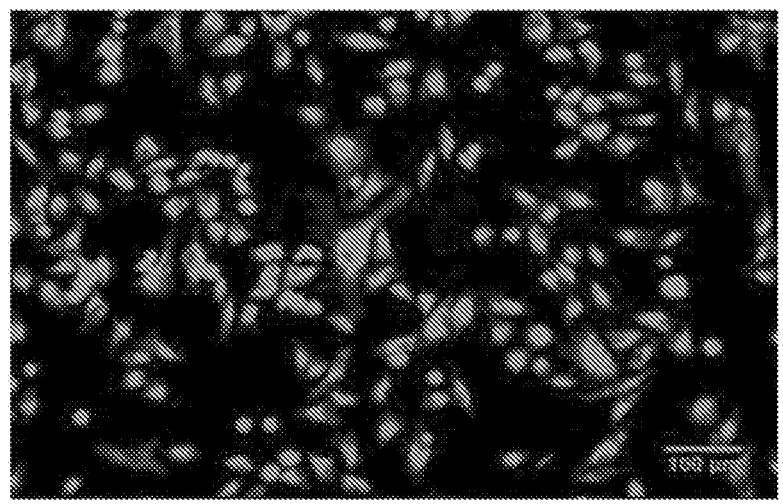

FIGS. 7A, 7B and 7C show fluorescence images of a sample, using three different fluorescent agents respectively.

Figure 7D:
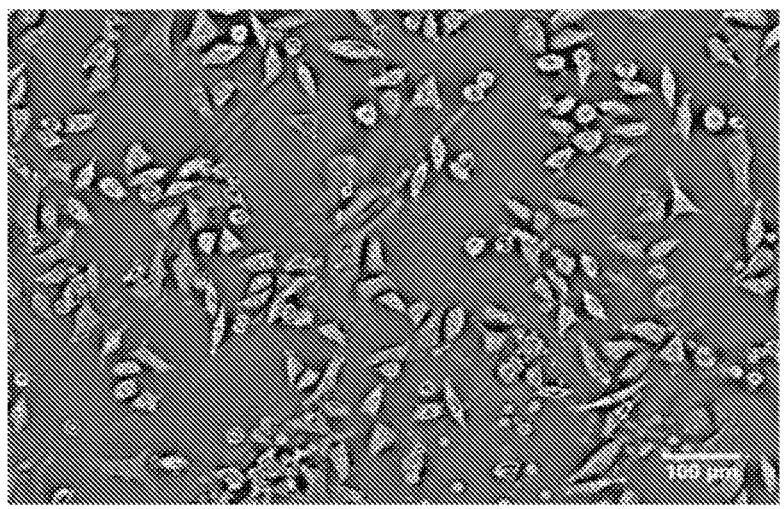

FIG. 7D is a phase image of the sample shown in FIGS. 7A to 7C.

DESCRIPTION OF PARTICULAR EMBODIMENTS

Figure 1A:
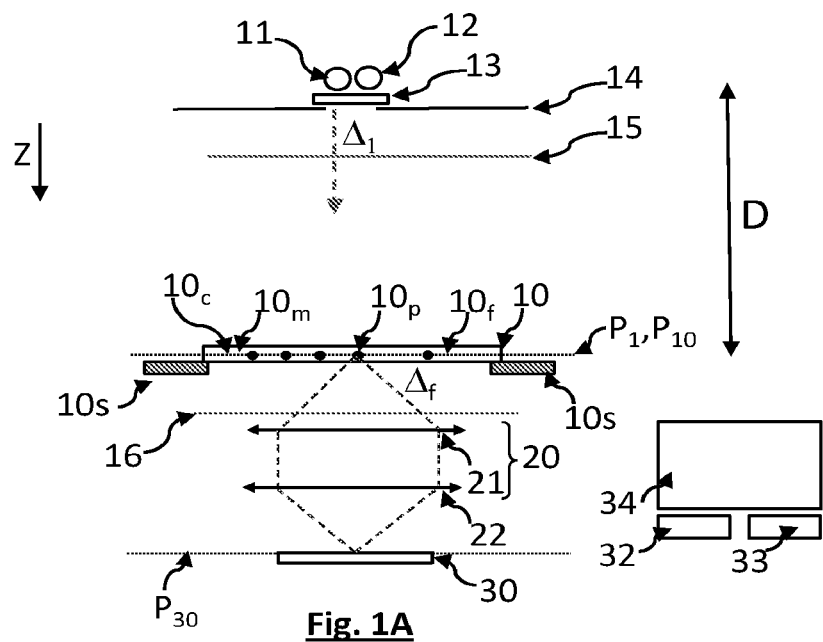
FIG. 1A shows a device of the invention in a first configuration.
Figure 1B:
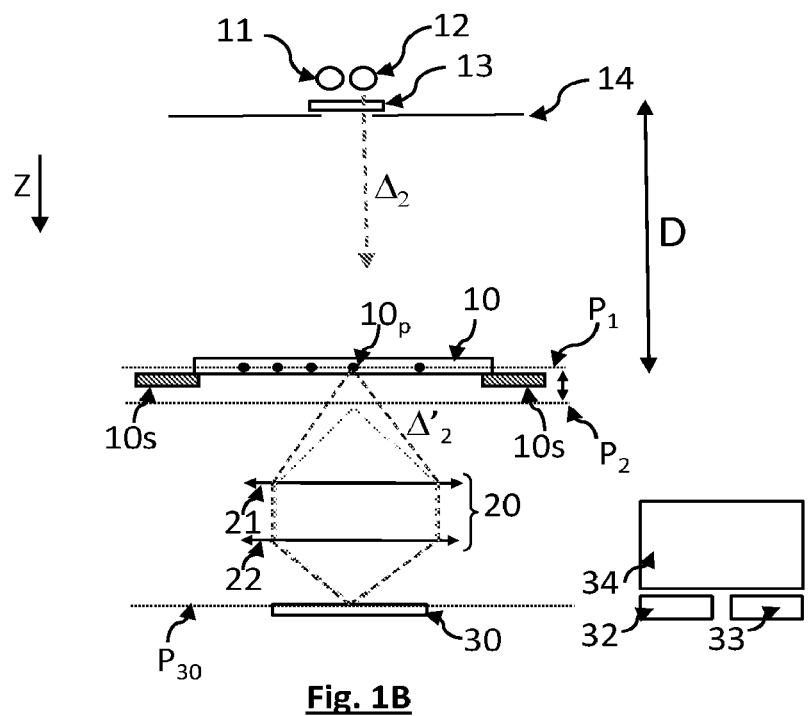
FIG. 1B shows the device shown in FIG. 1A according to a second configuration.

FIGS. 1A and 1B show a device allowing the invention to be implemented. The device includes a first light source 11 and a second light source 12. The first light source 11 is configured to emit a first light wave $\Delta_1$ in a first spectral band $\Delta\lambda_1$. The second light source 12 is configured to emit a second light wave $\Delta_2$ in a second spectral band $\Delta\lambda_2$. The second light wave $\Delta_2$ propagates along a propagation axis Z. In this example, the first light wave $\Delta_1$ propagates parallel to the second light wave $\Delta_2$, but this condition is not essential, as described with reference to FIG. 1C. The first spectral band $\Delta\lambda_1$ and the second spectral band $\Delta\lambda_2$ are centred on a first wavelength $\lambda_1$ and on a second wavelength $\lambda_2$, respectively.

The sample comprises a sample holder $10s$ that is configured to receive a sample 10, such that the sample is held on the holder $10s$ so as to lie in a plane, called the sample plane $P_{10}$. The sample 10 is a sample that it is desired to characterize. It especially comprises a liquid medium $10_m$, including particles $10_p$. The medium $10_m$ may be a buffer liquid. It may also include a bodily liquid, in the pure or diluted state. By bodily liquid, what is meant is a liquid generated by a living body. It may in particular be a question, nonlimitingly, of blood, of urine, of cerebrospinal fluid, of sperm, of lymph. By particle, what is especially meant is a cell, for example a blood cell, or a microorganism, for example a bacterium. The sample 10 is, in this example, contained in a fluidic chamber 15. The fluidic chamber 15 is for example a fluidic chamber of 100 µm thickness. The thickness of the fluidic chamber 15, and therefore of the sample 10, along the propagation axis Z, typically varies between 10 µm and 1 cm, and is preferably comprised between 20 µm and 500 µm.

The sample may be a transparent or translucent solid sample. It may for example be a thin slide of biological tissue, for example an anatomical-pathology slide, or even a dry extract of a liquid, for example a biological liquid.

The sample contains a fluorescent agent $10_f$ or fluorophore. It may be an exogenous agent, added to the sample prior to its observation, or an endogenous agent, naturally present in the sample. When it is illuminated in an excitation spectral band $\Delta\lambda_e$, the fluorescent agent $10_f$ emits a fluorescence light wave $\Delta_f$ in a fluorescence spectral band $\Delta\lambda_f$. An exogenous fluorescent agent is generally added to the object, so as to specifically bind to targets, for example a certain category of cells, or more generally to biological structures of interest, for example a nucleus of a cell, a DNA base, a tumour cell, or a biological structure comprising a ligand able to preferentially bind with the fluorescent agent. The fluorescent agent used may be IndoCyanine Green (or ICG). In this case, the excitation spectral band $\Delta\lambda_e$ is comprised between 750 nm and 800 nm, the fluorescence spectral band $\Delta\lambda_f$ being comprised between 820 nm and 870 nm. The fluorescent agent used may be DAPI (4', 6-diamidino-2-phenylindole). In this case, the excitation spectral band $\Delta\lambda_e$ is comprised between 350 nm and 400 nm, the fluorescence spectral band $\Delta\lambda_f$ being comprised between 430 nm and 530 nm. DAPI is known to bind to certain DNA bases. Its use for example allows DNA in a cell to be located. It is also possible to use a Hoechst stain, the optical properties of which are close to those of DAPI, but which is less toxic.

One of the objectives of the device 1 is to observe the sample 10 in a fluorescence mode. Thus, the first spectral band $\Delta\lambda_1$ corresponds to the excitation spectral band $\Delta\lambda_e$ of the fluorescent agent $10_f$ present in the sample 10.

The distance D between the second light source 12 and the sample 10 is preferably larger than 1 cm. It is preferably comprised between 2 and 30 cm. Advantageously, the second light source, seen by the sample, may be considered to be point-like. This means that its diameter (or its diagonal) is preferably smaller than one tenth, better still one hundredth of the distance between the sample and the light source. In FIG. 1A, the first light source 11 and the second light source 12 are light-emitting diodes. They may be associated with a diaphragm 14, or spatial filter. The aperture of the diaphragm is typically comprised between 5 μm and 1 mm, and preferably between 50 μm and 500 μm. In this example, the diaphragm has a diameter of 150 μm. In another configuration, the diaphragm may be replaced by an optical fibre, a first end of which is placed facing each light source and a second end of which is placed facing the sample 10. The device shown in FIGS. 1A and 1B also comprises a diffuser 13, placed between the light sources and the diaphragm 14. The use of such a diffuser allows constraints on the centrality of the light sources with respect to the aperture of the diaphragm 14 to be relaxed. The function of such a diffuser is to spread the light beam produced by an elementary light source 11 over a cone of angle α. Preferably, the scattering angle α varies between 10° and 80°. Alternatively, the first and/or second light source may be a laser source, such as a laser diode. When a light source is a laser diode, it is not useful to associate it with a spatial filter or a diffuser.

In the example shown in FIG. 1A, the sample 10 is placed between the first light source 11 and the image sensor 30. However, this is not essential. In the example shown in FIG. 1C, the first light source 11 is placed in a half-space bounded by the sample plane $P_{10}$ and comprising the image sensor 30.

Preferably, the first spectral band $\Delta\lambda_1$ and/or the second spectral band $\Delta\lambda_2$ have a bandwidth narrower than 200 nm, or even than 150 nm or 100 nm. By spectral bandwidth, what is meant is a full width at half-maximum of the spectral band.

According to another embodiment, the device comprises a wide-spectral-band light source called the main light source, which emits white light. The illumination of the sample in the first spectral band $\Delta\lambda_1$ and in the second spectral band $\Delta\lambda_2$ is respectively obtained by placing a first bandpass filter, defining the first spectral band, and a second bandpass filter, defining the second spectral band, between the main light source and the sample. The first light source 11 is obtained by associating the main light source and the first bandpass filter. The second light source 12 is obtained by associating the main light source and the second bandpass filter. The width of the first and second spectral bands are respectively determined by the respective passbands of the first and second bandpass filters.

The sample 10 is placed between the second light source 12 and an image sensor 30. The latter preferably lies parallel, or substantially parallel, to the plane $P_{10}$ in which the sample 10 lies. The expression substantially parallel means that the two elements may not be rigorously parallel, an angular tolerance of a few degrees, lower than 20° or 10°, being allowed. In this example, the sample lies in a plane $P_{10}$ perpendicular to the propagation axis Z. The first light source 11 may be placed:

in a half-space bounded by the sample plane $P_{10}$ and comprising the second light source 12 or in a half-space bounded by the sample plane $P_{10}$ and comprising the image sensor 30.

The image sensor 30 is configured to form an image of the sample in a detection plane $P_{30}$. In the example shown, the image sensor 30 comprises a CCD or CMOS pixel matrix array. The detection plane $P_{30}$ preferably lies perpendicular to the propagation axis Z of the incident second light wave $\Delta_2$. In the example shown, the image sensor 30 is an IDS UI-1942LE-M CMOS sensor comprising 3840×2748 pixels, the size of each pixel being 1.67 μm×1.67 μm.

The image sensor 30 is optically coupled to the sample 10 by an optical system 20. In the example shown, the optical system comprises an objective 21 and a tube lens 22. The optical system 20 is chromatic: for a given image focal plane, in the present case coincident with the detection plane $P_{30}$, the position of the object focal plane is dependent on wavelength. Reciprocally, for a given object plane, in the present case coincident with the sample plane $P_{10}$, the position of the image plane is dependent on wavelenght. Thus, when two wavelengths are separated by 100 nm, the object planes (or image planes) corresponding to each wavelength are spaced apart by at least 10 μm, and preferably by at least 20 μm or 30 μm, or indeed 50 μm, respectively. In this example, the objective 21 is a Motic CCIS EF-N Plan Achromat 10× objective, of 0.25 numerical aperture. It is optically coupled to the lens 22, the latter being the origin of the chromatic aberrations of the optical system 20 that result in the spacing between the object planes (or image planes) being wavelength-dependent. The lens is, in this example, the following lens: LBF254-050-N-BK7 Best Form Lens, Ø1", f=50 mm.

ae device in a first configuration in which the sample is illuminated, by the first light source, in the first spectral band $\Delta\lambda_1$, which corresponds to the excitation spectral band $\Delta\lambda_f$ of the fluorescent agent $10_f$. Under the effect of this illumination, the fluorescent agent emits a fluorescence wave $\Delta_f$ in the fluorescence spectral band $\Delta\lambda_f$. The optical system 20 is placed such that, in the fluorescence spectral band $\Delta\lambda_f$ the first object focal plane $P_1$ corresponds to the plane $P_{10}$ in which the sample 10 lies, this corresponding to the plane in which the fluorescence light wave $\Delta_f$ is emitted. The conjugate image focal plane of the first object focal plane $P_1$ is the detection plane $P_{30}$. Thus, in this configuration, the image sensor 30 acquires a clear first image $I_1$ of the sample, this image being representative of the fluorescence of the sample 10. It allows a spatial distribution of the fluorescent agent $10_f$ in the sample to be observed.

In this configuration, an optical filter 15, called the excitation filter, may be placed between the first light source 11 and the sample 10. The excitation filter 15 allows the first spectral band $\Delta\lambda_1$ to be adjusted such that the light wave $\Delta_1$ illuminating the sample corresponds to all or some of the excitation spectral band $\Delta\lambda_e$.

An optical filter 16, called the fluorescence filter, may be placed between the sample 10 and the image sensor 30. The fluorescence filter 16 allows the light wave detected by the image sensor 30 to be limited to the fluorescence spectral band $\Delta\lambda_f$. This especially makes it possible to prevent parasitic light not originating from fluorescence of the sample from degrading the image acquired by the image sensor. The optical filter 16 has a fluorescence passband, corresponding to the fluorescence spectral band $\Delta\lambda_f$. It may also be a question of a multi-band bandpass filter the passband of which includes both the fluorescence spectral band $\Delta\lambda_f$ and a second spectral band $\Delta\lambda_2$, which is described below. By multi-band bandpass filter, what is meant is a filter the passband of which includes distinct passbands that are spaced apart from one another. It may also be a question of a high-pass filter that lets wavelengths located beyond the excitation spectral band $\Delta\lambda_e$ pass and that blocks wavelengths in the excitation spectral band.

In another configuration, shown in FIG. 1B, the sample is illuminated by the second light source 12, in the second spectral band $\Delta\lambda_2$, the latter being different from the fluorescence spectral band $\Delta\lambda_f$ of the fluorescent agent $10_f$. Preferably, the second spectral band is centred on a wavelength $\lambda_2$ that is offset by at least 100 nm, or even 150 nm or even 200 nm from the central wavelength $\Delta_f$ of the fluorescence spectral band. Specifically, it is preferable for the fluorescence spectral band $\Delta\lambda_f$ and the second spectral band $\Delta\lambda_2$ to not overlap, or to overlap only marginally. For example, more than 80%, or more than 90%, of the light intensities emitted in each of the spectral bands, respectively, does not overlap. Considering each spectral band to be bounded by a lower limit and an upper limit, defining the full width at half-maximum of the spectral band, it is preferable for the upper limit of a spectral band to be distant, by at least 50 nm or even at least 100 nm, from the lower limit of another spectral band.

The optical system 20 is such that, in the second spectral band $\Delta\lambda_2$, the second object focal plane $P_2$ is offset with respect to the first object focal plane $P_1$, the latter corresponding to the plane $P_{10}$ in which the sample 10 lies. The image focal plane, conjugate of the second object focal plane $P_2$, is the detection plane $P_{30}$. Thus, in this configuration, the image sensor 30 acquires a defocused second image $I_2$ of the sample 10, in the second spectral band $\Delta\lambda_2$. FIG. 1B shows the second object focal plane $P_2$, and the sample plane $P_{10}$, the latter being coincident with the first focal plane $P_1$. In this configuration, the image sensor 30 is exposed to a light wave $\Delta'_2$, called the exposure light wave. The acquired image contains interference patterns (or "diffraction patterns") formed by:
  a portion of the second light wave $\Delta_2$ emitted by the second light source 12, and having passed through the sample without interacting with the latter;

diffracted waves, formed by diffraction of a portion of the second light wave $\Delta_2$ in the sample.

The second image $I_2$ acquired by the image sensor 30 contains interference patterns (or diffraction patterns) that are representative of the sample 10, or of the particles $10_p$ contained in the latter. Generally, the second image $I_2$ acquired by the image sensor 30 is representative of the structure of the sample.

A processor 32, for example a microprocessor, is able to process the second image $I_2$ acquired by the image sensor 30. In particular, the processor is a microprocessor 32 connected to a programmable memory 33 in which a sequence of instructions for carrying out the image-processing and computing operations described in this description is stored. The processor 32 may be coupled to a screen 34 allowing images acquired by the image sensor 30 or computed by the processor 32 to be displayed.

The defocused second image $I_2$ acquired by the image sensor 30 in the second configuration, does not allow a precise representation of the observed sample to be obtained. Conventionally, in the holography field, a holographic reconstruction operator h may be applied to the second image $I_2$ so as to calculate a complex expression A representative of the light wave $\Delta'_2$ to which the image sensor is exposed, at any point of spatial coordinates (x,y,z), and in particular in a plane, called the reconstruction plane $P_Z$, located at a distance |z|, called the reconstruction distance, from the image sensor 30. The reconstruction plane is preferably the plane $P_{10}$ in which the sample 10 lies. The complex expression A(x,y,z) at the point of coordinates (x,y,z) is obtained from the second image $I_2$, by calculating the convolution product given by the following equation:

$$A(x,y,z)=I_2(x,y,z)*h, \text{ the symbol * representing the convolution operator.}$$

The coordinates (x,y) designate a planar position in a radial plane perpendicular to the propagation axis Z. The z coordinate designates a coordinate along the propagation axis Z. Before application of the reconstruction operator, the second image $I_2$ may be normalized or undergo pre-processing before the convolution by the reconstruction operator.

The function of the reconstruction operator h is to describe the propagation of the light between the image sensor 30 and a point, of coordinates (x,y,z), located at a distance |z| from the image sensor. The complex expression A of the exposure light wave $\Delta'_2$, at any point of spatial coordinates (x,y,z), is such that: $A(x,y,z)=M(x,y,z)e^{j\varphi(x,y,z)}$ where M(x,y,z) and $\varphi$(x,y,z) are the modulus and phase of the exposure light wave $\Delta'_2$, at the point of coordinates (x,y,z), respectively. Thus:
  M(x,y,z)=abs[A(x,y,z)]; and
  $\varphi$(x,y,z)=arg[A(x,y,z)].
The operators abs and arg designate the modulus and argument, respectively.

The complex expression A is a complex quantity the argument and the modulus of which are representative of the phase and amplitude of the exposure light wave detected by the image sensor 30, respectively. The product of convolution of the second image $I_2$ and the reconstruction operator h may allow a complex image $A_z$ that represents a spatial distribution of the complex expression A in a reconstruction plane $P_Z$ lying at a distance |z| from the detection plane $P_{30}$ to be obtained.

The complex image $A_z$ corresponds to a complex image of the sample in the reconstruction plane $P_Z$. It also represents a two-dimensional spatial distribution of the complex expression A describing the exposure wave $\Delta'_2$. Such methods, which are referred to as "holographic reconstruction" methods, especially allow an image $M_Z$ of the modulus or an image $\varphi_Z$ of the phase of the complex expression defining the exposure light wave $\Delta'_2$ to be reconstructed in the reconstruction plane. The image of the modulus or of the phase of the exposure light wave $\Delta'_2$ is obtained using the following expressions:

$M_Z=\mod(A_z)$ and $\varphi_Z=\arg(A_z)$, respectively.

The reconstruction operator is for example the Fresnel-Helmholtz function, such that:

$$h(x, y, z) = \frac{1}{j\lambda z} e^{j2\pi \frac{z}{\lambda}} \exp\left(j\pi \frac{x^2 + y^2}{\lambda z}\right).$$

Examples of holographic reconstructions are described in the publication Seo S et al, "High-Throughput lens-free blood analysis on a chip", Anal Chem. 2010 Jun. 1; 82(11): 4621-4627, or even in document WO2017162985.

When the sample is transparent, the reconstructed image is preferably an image $\varphi_Z$ of the phase of the complex expression of the light wave $\Delta'_2$ striking the image sensor 30. When the reconstruction plane is plane $P_{10}$ in which the sample lies, such an image gives a relatively precise visual representation of the structure of the sample.

Thus, the invention allows a first image $I_1$ that is representative of the fluorescence of the sample, and a second image $I_2$ that, after holographic reconstruction, is representative of the structure of the sample 10, to be obtained. A noteworthy aspect of the invention is that between the acquisition of the first image and the acquisition of the second image, neither the sample 10, nor the image sensor 30, nor the optical system 20 are moved. This avoids recourse to means for moving and positioning the optical system. It is thus possible to successively acquire a first image and a second image of the sample by successively activating the first light source 11, then the second light source 12. When the first image $I_1$ is acquired, it is preferable for the second light source 12 to be turned off, so as to prevent parasitic light from degrading the first image. It is also desirable for the first light source 11 to be turned off when the second image $I_2$ is acquired. Preferably, the first image and the second image are acquired sequentially. The device 1 allows bimodal observation of the sample in a simple way, requiring no deustment of a focal plane of the optical system 20 between implementation of the two modes. The exposure time of the first image may be longer than the exposure time of the second image, because the intensity of the fluorescence light wave is generally low.

When a multi-band optical filter such as described above is used, all the components of the device, including the sample 10, may remain stationary, no movement needing to be provided for between the acquisition of the first image $I_1$ and of the second image $I_2$. This allows a rapid switch between the acquisition of the first image and the acquisition of the second image.

Figure 1C:
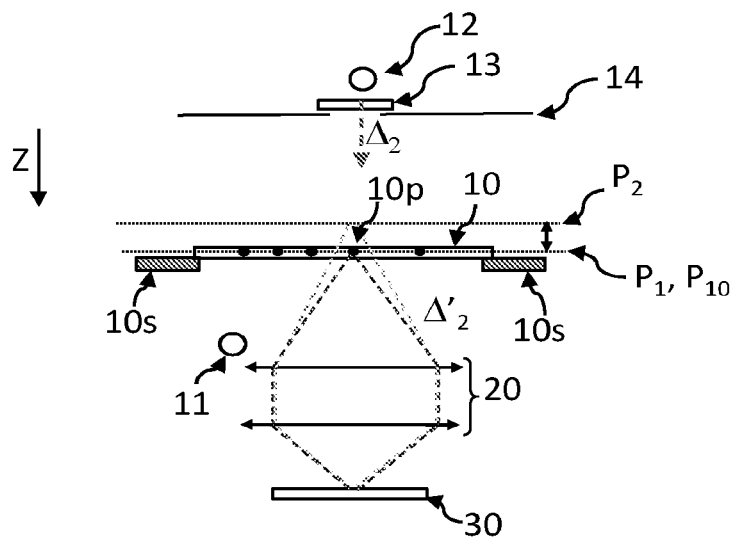
FIG. 1C is a variant of the device shown in FIGS. 1A and 1B.

FIG. 1C shows a configuration also allowing a second image to be acquired. Whereas in FIG. 1B, the object focal plane $P_2$ in the second spectral band $\Delta\lambda_2$ is placed between the sample and the optical system 20, in FIG. 1C, the object focal plane $P_2$ is placed between the sample 10 and the second light source 12.

Figure 1D:
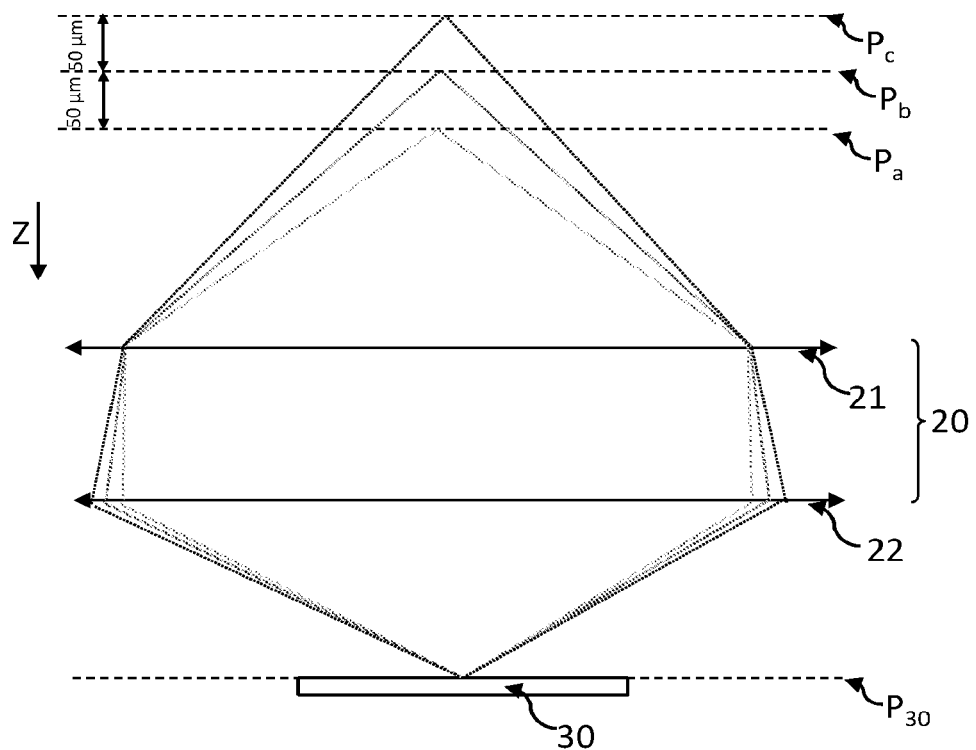
FIG. 1D illustrates three object planes of an optical system, said planes being spaced apart from one another, each object plane corresponding to one spectral band.

FIG. 1D shows three object focal planes of an optical system 20 suitable for implementation of the invention. The objective has three object focal planes $P_a$, $P_b$, $P_c$, the focal planes corresponding to a blue spectral band (for example 450 nm±20 nm), to a green spectral band (for example 550 nm±20 nm) and to a red spectral band (for example 650 nm±20 nm), respectively. The distance between two adjacent focal planes is for example comprised between 50 µm and 100 µm. Preferably, the chromatic optical system 20 is configured such that two object focal planes corresponding to two spectral bands separated by 100 nm are distant from each other by at least 20 µm, or even at least 30 µm or at least 50 µm, respectively.

FIG. 2A shows images of a fluorescent sample, said images having been successively acquired while the sample was gradually moved away from the first focal plane $P_1$. The offset with respect to the first plane $P_1$, expressed in µm, is indicated in each image. For each image, a signal-to-noise ratio SNR relating to each image was calculated. This signal-to-noise ratio corresponds to the maximum intensity, in the image, divided by an estimation of a noise level of the image. FIG. 2B shows the variation in the SNR ratio as a function of the offset with respect to the first object plane $P_1$. This shows that the fluorescence image $I_1$ must preferably be acquired when the sample is placed in the object focal plane of the optical system corresponding to the fluorescence spectral band. An offset, even a minimal offset, is prejudicial to the quality of the fluorescence image obtained.

Implementation of the invention is somewhat summarized in FIGS. 3A to 3D. In this example, the sample was composed of neurons stained with DAPI. FIG. 3B shows a fluorescence image of the sample ($\Delta\lambda_f$ centred on 452 nm), called the first image $I_1$, the device being configured as described with reference to FIG. 1A, the light source being a light-emitting diode emitting in the UV. FIG. 3A shows a defocued second image of the sample, acquired whilst the device was placed as described with reference to FIG. 1B, in a spectral band $\Delta\lambda_2$ centred on 543.5 nm and of 2.1 nm spectral width. In this example, the object focal plane of the sample, in the second spectral band $\Delta\lambda_2$, was distant by 50 µm from the object focal plane of the sample in the fluorescence spectral band $\Delta\lambda_r$ of the DAPI. A holographic reconstruction algorithm was applied to the second image of the sample, using the method described in patent application WO2017162985 and more particularly in the steps 110 to 160 described in the latter. The reconstruction was carried out in the plane in which the sample lay, said plane being coincident with the object focal plane $P_1$ of the first mode. FIG. 3C shows the phase image of the complex expression calculated in the sample plane $P_{10}$. The various neuronal structures appear clearly. Thus, the phase image allows exploitable information on the structure of the sample to be obtained.

FIG. 3D is a superposition of the phase image shown in FIG. 3C and the fluorescence image shown in FIG. 3B. This allows the staining of the nuclei of the neurons with DAPI to be observed.

FIG. 4 illustrates the main steps of the method:
step 100: placing the sample on the sample holder;
step 110: illuminating the sample in the first spectral band and acquiring a first image $I_1$ of the sample, corresponding to the fluorescence mode;
step 120: illuminating the sample in the second spectral band, and acquiring a defocused second image $I_2$ of the sample;
step 130: applying, to the second image, a holographic reconstruction operator in order to obtain, preferably, a phase image of the sample, in order to obtain information on the structure of the sample;

step 140: superposing the fluorescence image and the image resulting from the holographic reconstruction.

The chronological order in which steps 110 and 120 are implemented is unimportant.

In another experimental trial, living Madin-Darby Canine Kidney (MDCK) cells cultivated in an incubator were stained with the DNA-specific fluorescent agent Hoechst 33342. Six hours after staining, a first fluorescence image of the sample was acquired. The sample was then illuminated in the near UV, in order to make it emit a fluorescence light wave in the spectral band $\Delta\lambda_f$ centred on 452 nm. A defocused second image of the sample was also acquired by illuminating the latter in a second spectral band $\Delta\lambda_2$ centred on 543.5 nm and of 2.1 nm bandwidth. To this second spectral band corresponded an object focal plane that was distant by 60 µm from the object focal plane that corresponded to the fluorescence wavelength of the fluorescent agent. The method described with reference to FIGS. 3B and 3C was applied to the defocused image of the sample, so as to obtain a phase image representative of the structure of the sample. The fluorescence image and the phase image were then superposed. This operating mode was repeated a number of times, at regular intervals (i-e every 8 hours and 20 minutes), over a total duration of 75 hours. FIGS. 5A, 5B and 5C show the structural images of the sample (phase images), the fluorescence images of the sample and the superpositions of the fluorescence and structural images, respectively.

According to an embodiment, the optical system is such that the object focal plane of the optical system is coincident with the sample plane, or substantially coincident with the sample plane, in a wide fluorescence spectral band. By substantially coincident, it is meant coincident within a ±30 µm margin. By wide spectral band, it is meant a spectral band which band width is at least 150 µm wide, or preferably at least 200 µm wide. In a second spectral band $\Delta\lambda_2$, the object focal plane of the optical system is offset with respect to the sample plane $P_{10}$, the offset being larger than 50 µm. Due to the width of the fluorescence spectral band, this embodiment makes it possible to get a fluorescence image of different fluorescent agents, sequencially or simultaneously.

FIG. 6A shows a curve which is representative of the chromatism of the optical system 20. The optical system 20 comprises the previously described Motic objective 21, as well as a doublet tube lens 22. FIG. 6A shows the variation of the focal distance as a function of the wavelenght. The x-axis corresponds to the wavelenght. The y-axis corresponds to the variation of the focal distance, with respect to a focused configuration, at a wavelenght of 420 nm.

Between 440 nm and 650 nm, the variation of the focal distance is not significant: the focal distance varies within a ±30 µm margin around 60 µm. Below 440 nm, the variation of the focal distance is more significant.

The device shown in FIGS. 6C and 6D makes use of such an optical system. In the configuration shown in FIG. 6C, the device enables a clear (focused) fluorescence image to be acquired. In the configuration shown in FIG. 6D, the device enables a defocused image of the sample to be acquired.

In the device shown in FIG. 6C, the first light source 11 is coupled to a collimation lens 19. Downstream the collimation lens 19, an excitation filter 15 allows the first spectral band $\Delta\lambda_1$ to be adjusted. As a result, the light wave $\Delta_1$ illuminates the sample 10 in all or part of the excitation spectral band of different fluorescent agents $10_{f1}$, $10_{f2}$, $10_{f3}$. The excitation filter 15 includes three elementary excitation spectral bands $\Delta\lambda_{e1}$, $\Delta\lambda_{e2}$, $\Delta\lambda_{e3}$. The elementary excitation spectral bands $\Delta\lambda_{e1}$, $\Delta\lambda_{e2}$, $\Delta\lambda_{e3}$ are different from each other.

The elementary excitation spectral bands $\Delta\lambda_{e1}$, $\Delta\lambda_{e2}$, $\Delta\lambda_{e3}$ are shown in FIG. 6B. They correspond to the excitation spectral band of DAPI (previously described) $10_{f1}$, of the Green Fluorescent Protein (GFP) $10_{f2}$, and of the mCherry protein $10_{f3}$ respectively.

The first light source 11 includes three elementary light sources $11_1$, $11_2$, $11_3$. The first light source is configured to emit the first light wave $\Delta_1$ in the elementary excitation spectral bands $\Delta\lambda_{e1}$, $\Delta\lambda_{e2}$, $\Delta\lambda_{e3}$, simultaneously or sequentially. When using a monochrome image sensor, the elementary light sources should be activated sequentially.

As shown in FIG. 1C, the first light wave $\Delta_1$ propagates toward a dichroic mirror 18. The transmission spectral band of the dichroic mirror 18 is shown in FIG. 6B. The transmission spectral band of the dichroic mirror includes three elementary spectral bands $\Delta\lambda_{f1}$, $\Delta\lambda_{f2}$, $\Delta\lambda_{f3}$, which comprise emission peaks of DAPI, GFP and mCherry respectively. The dichroic mirror 18 reflects the three excitation spectral bands $\Delta\lambda_{e1}$, $\Delta\lambda_{e2}$, $\Delta\lambda_{e3}$ toward the sample 10. Should the particles $10_p$ of the sample 10 be stained with all or part of the fluorescent agents $10_{f1}$, $10_{f2}$, $10_{f3}$, a fluorescent light wave $\Delta_f$ is emitted, in all or part of the fluorescence spectral bands $\Delta\lambda_{f1}$, $\Delta\lambda_{f2}$, $\Delta\lambda_{f3}$. Due to the transmission spectral band of the dichroic miroir 18, the fluorescent light wave $\Delta_f$ is transmitted by the mirror 18 towards the image sensor 30.

The optical system 20 is configured such that, in each of the fluorescence spectral bands $\Delta\lambda_{f1}$, $\Delta\lambda_{f2}$, $\Delta\lambda_{f3}$, the object plane is coincident (or substantially coincident) to the sample plane $P_{10}$. Depending on the elementary light source which is activated, first fluorescence images $I_1$ are obtained, in different fluorescence spectral bands. Each first image $I_1$ is an clear image. The fluorescence images $I_1$ may be acquired successively. Each fluorescence image $I_1$ show the spatial distribution of at least one fluorescent agent within the sample 10.

The image sensor is an IDS UI-1480SE monochrome CMOS sensor, comprising 2560×1920 pixels, the size of each pixel being 2.2 µm×2.2 µm.

In a second configuration, a defocused second image $I_2$ is acquired by the image sensor 30, as shown in FIG. 6D. In this configuration, the sample 10 is illuminated by a second light source 12, in a second spectral band $\Delta\lambda_2$. The second light source 12 includes:

an illuminating light source 12';
a fiber optics $12_f$ extending between a proximal end $12_p$ and a distal end $12_d$.

The proximal end $12_p$ of the fiber optics $12_f$ is placed facing the illuminating source 12'.

The second light source 12 is configured to emit a second light wave $\Delta_2$ in a second spectral band $\Delta\lambda_2$. The second light wave $\Delta_2$ propagates along a propagation axis Z. A pass band filter 17 defines a second spectral band $\Delta\lambda_2$ of the second light wave $\Delta_2$. In this example, the second spectral band $\Delta\lambda_2$ in centred on 40 nm. The bandwidth of the the second spectral band $\Delta\lambda_2$ is 10 nm.

The optical system 20 is placed such that, in the second spectral band $\Delta\lambda_2$, the second object focal plane $P_2$ is offset with respect to the first object focal plane $P_1$, the latter corresponding to the plane $P_{10}$ in which the sample 10 lies. The image focal plane, conjugate of the second object focal plane $P_2$, is the detection plane $P_{30}$. Thus, in this configuration, the image sensor 30 acquires a defocused second image $I_2$ of the sample 10, in the second spectral band $\Delta\lambda_2$.

Alternatively, in the second spectral band $\Delta\lambda_2$, the second object plane $P_2$ is coincident to the sample plane $P_{10}$ and the second image plane is offset with respect to the detection plane $P_{30}$.

In this example, the defocus distance is 70 µm.

FIGS. 7A, 7B and 7C show first images $I_1$ acquired by the image sensor 30 during the activation of the elementary light sources $11_1$, $11_2$ and $11_3$ respectively. The sample 10 included Hela Cells. The sample Cell had been previously stained with three fluorescent agent $10_{f1}$ (DAPI), $10_{f2}$ (GFP) and $10_{f3}$ (mCherry). FIGS. 7A, 7B and 7C show the spatial distribution of the three fluorescent agents respectively. FIG. 7D shows a phase image of the cells. The phase image of the cells is based on the defocused image $I_2$, as previously described (steps 120 and 130).

A noticeable feature of this embodiment is that it enables clear (i-e in-focus) fluorescence images of different fluorescence agents to be acquired successively or simultaneously.

The device, because of the absence of adjustment of the focal planes between two image acquisitions in the various modes, is compact and may easily be placed inside an incubator. It allows samples to be observed with a large field of observation. This field of observation may for example extend over an area of 4 mm², this allowing simultaneous observation of many biological species. The area depends on the magnification of the optical system.

The invention claimed is:

1. A method for observing a fluorescent sample, lying in a sample plane, the sample comprising a fluorescent agent configured to emit a fluorescence light wave, in a fluorescence spectral band, when it is illuminated by an excitation light wave, in an excitation spectral band, the method comprising:
   a) illuminating the sample using a first light source, in a first illumination spectral band, the first illumination spectral band lying in the excitation spectral band, and acquiring a first image of the sample, in the fluorescence spectral band, using an image sensor, the image sensor defining a detection plane;
   b) illuminating the sample using a second light source, in a second spectral band, outside of the fluorescence spectral band, the sample lying between the second light source and the image sensor, and acquiring a second image of the sample, in the second spectral band, using the image sensor;
   the image sensor being coupled to an optical system placed between the image sensor and the sample, the optical system being such that:
   in the fluorescence spectral band, the object plane of the optical system is coincident with the sample plane; and
   in the second spectral band, at least one of
      the object plane of the optical system is offset with respect to the sample plane, and
      the image plane, of the optical system is offset with respect to the detection plane,
   the offset being larger than 20 µm;
   wherein:
   the first image is a focused image of the sample, which image is representative of a fluorescence of the sample;
   the second image is a defocused image of the sample, which image is representative of a structure of the sample; and
   the image sensor, the optical system and the sample remain stationary between the acquisition of the first image and the acquisition of the second image.

2. The method according to claim 1, comprising:
   c) applying a holographic reconstruction operator to the second image, so as to obtain a reconstructed image of the sample in a reconstruction plane.

3. The method according to claim 1, wherein the second spectral band is offset, with respect to the fluorescence spectral band, by at least 150 nm and preferably by at least 200 nm.

4. The method according to claim 1, wherein, in the second spectral band, the object focal plane is offset from the sample plane by a distance smaller than 1 mm, and preferably by a distance smaller than 500 µm.

5. The method according to claim 1, wherein:
   the first light source is placed in a half-space bounded by the sample plane and comprising the image sensor; or
   the first light source is placed in a half-space bounded by the sample plane and comprising the second light source.

6. The method according to claim 1, wherein a) and b) are carried out successively, a) being carried out before b) or vice versa.

7. The method according to claim 1, wherein the second spectral band is at least 150 nm or at least 200 nm wide, so as to include fluorescence peaks of different fluorescent agents.

8. A device for observing a fluorescent sample, the sample being configured to emit a light wave in a fluorescence spectral band when it is illuminated in an excitation spectral band, the device comprising:
   a first light source configured to emit a light wave in a first spectral band lying in an excitation spectral band of the sample;
   a second light source configured to emit a light wave in a second spectral band outside of the fluorescence spectral band of the sample;
   an image sensor that is optically coupled to an optical system, the image sensor defining a detection plane; and
   a holder intended to receive the sample, such that the sample lies in a sample plane, the latter lying between the optical system and the second light source;
   the optical system defining:
      in the fluorescence spectral band, a first object plane that is coincident with the sample plane; and
      in the second spectral band, at least one of a second object plane that is distant from the sample plane by at least 20 µm and a second image plane that is distant from the detection plane by at least 20 µm;
   wherein the image sensor is configured to acquire, without moving the sample or the image sensor or the optical system:
      a clear image of the sample, in the fluorescence spectral band, when the sample is illuminated by the first light source; and
      a defocused image of the sample, in the second spectral band, when the sample is illuminated by the second light source.

9. The device according to claim 8, wherein the distance between the first object plane and the second object plane is smaller than 1 mm, and preferably smaller than 500 µm.

10. The device according to claim 8, comprising a processor configured to apply a holographic reconstruction operator to an image acquired by the image sensor, so as to reconstruct an image representative of the sample, in a reconstruction plane distant from a detection plane in which the image sensor lies, and preferably in the sample plane.

11. The device according to claim 8, comprising a filter, lying between the sample and the image sensor, having a fluorescent pass band, corresponding to the fluorescence spectral band.

12. The device according to claim 11, wherein the filter has an auxiliary passband, distinct from the fluorescence passband, corresponding to the second spectral band.

13. The device according to claim 11, wherein the fluorescence passband of the filter has a bandwidth narrower than 100 nm.

14. The device according to claim 8, wherein:
the first light source is placed in a half-space bounded by the sample plane and comprising the image sensor; or
the first light source is placed in a half-space bounded by the sample plane and comprising the second light source.

15. The device according to claim 8, wherein the device is configured to form an in-focus image of the sample in a spectral band which is at least 150 nm or at least 200 nm wide.

* * * * *